United States Patent
Yamane et al.

(10) Patent No.: US 7,485,720 B2
(45) Date of Patent: Feb. 3, 2009

(54) CELLULOSE-TYPE MATERIAL (75) Inventors: Chihiro Yamane, Fuji (JP); Kunihiko Okajima, Fuji (JP); Makiko Otsuka, Kyoto (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 306 days.

(21) Appl. No.: 10/494,684

(22) PCT Filed: Nov. 7, 2002

(86) PCT No.: PCT/JP02/11615

§ 371 (c)(1),
(2), (4) Date: May 5, 2004

(87) PCT Pub. No.: WO03/040189

PCT Pub. Date: May 15, 2003

(65) Prior Publication Data

US 2004/0267006 A1 Dec. 30, 2004

(30) Foreign Application Priority Data

Nov. 8, 2001 (JP) .............................. 2001-379299

(51) Int. Cl.
- C07H 1/00 (2006.01)
- C12P 19/04 (2006.01)
- A61K 31/715 (2006.01)
- C08B 1/00 (2006.01)

(52) U.S. Cl. .................... 536/124; 536/56; 514/57; 435/101

(58) Field of Classification Search .................. 536/56, 536/124; 514/57; 435/101
See application file for complete search history.

(56) References Cited

U.S. PATENT DOCUMENTS 5,144,021 A    9/1992   Arie et al.

FOREIGN PATENT DOCUMENTS

| EP | 0 228 779 A2 | 7/1987 |
| EP | 0 831 101 A1 | 3/1998 |
| EP | 0 938 925 A1 | 9/1999 |
| EP | 0 987 296 A1 | 3/2000 |
| EP | 0 938 925 B1 | 8/2005 |
| EP | 0 987 296 B1 | 12/2006 |
| JP | 62-265990 A | 11/1987 |
| JP | 63-74490 A | 4/1988 |
| JP | 63-202394 A | 8/1988 |
| JP | 2-238888 A | 9/1990 |
| JP | 5-1718 B2 | 1/1993 |
| JP | 6-43443 B2 | 6/1994 |

(Continued)

OTHER PUBLICATIONS

Science, vol. 223, pp. 283-285, Jan. 1984.

(Continued)

*Primary Examiner*—Shaojia Anna Jiang
*Assistant Examiner*—Everett White
(74) *Attorney, Agent, or Firm*—Birch, Stewart, Kolasch & Birch, LLP (57) ABSTRACT

A spherical cellulose material wherein the cellulose material is a water-insoluble polysaccharide formed by β-1,4-type sugar chain linkages, the degree of crystallinity is 70% or greater, and macrofibrils are formed radially from the center to the periphery.

4 Claims, 5 Drawing Sheets

FOREIGN PATENT DOCUMENTS

| | | | |
|---|---|---|---|
| JP | 7-184675 A | | 7/1995 |
| JP | 7-184677 A | | 7/1995 |
| JP | 9-94094 A | | 4/1997 |
| JP | 2877676 B2 | | 1/1999 |
| JP | 2971024 B2 | | 8/1999 |
| JP | 2001-321164 A | | 11/2001 |
| JP | 2001321164 A | * | 11/2001 |
| WO | WO-89/12107 A1 | | 12/1989 |
| WO | WO 96/33222 A1 | | 10/1996 |

OTHER PUBLICATIONS

VanderHart, D.L. et al., Macromolecules, vol. 17, pp. 1465-1472 (1984).

Brown, W. et al., European Polymer Journal, vol. 1, pp. 1-10 (1965).

Kamide, K. et al., Polymer Journal, vol. 17, No. 5, pp. 707-711 (1985).

Watanabe, K. et al. Cellulose, vol. 5, pp. 187-200 (1998).

Hestrin, S. et al., Biochem. Journal, vol. 58, pp. 345-352 (1954).

K. Fujiwara, English translation of Abstract of "Research on microbial enhanced oil recovery technique by using cellulose producing microbe", Cellulose Communications vol. 8, No. 3, pp. 127-131 (2001).

Shimada, Akihiko, "Extracellular polysaccharides which Enterobacter sp. produces under anaerobic condition", Viva Origino, vol. 23, No. 1, pp. 52-53 (1995).

* cited by examiner

CELLULOSE-TYPE MATERIAL

TECHNICAL FIELD

The present invention relates to cellulose materials and polysaccharide having new structures and characteristics, produced by bacteria, their culture methods and their uses.

BACKGROUND ART

As cellulose material producing bacteria, *Acetobacter* strains (*Acetobacter*) such as *Acetobacter xylinum* subsp. *sucrofermentans* represented by the BPR2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142 and *Acetobacter xylinum* ATCC10821, *Agrobacterium, Rhizobium, Sarcina, Pseudomonas, Achromobacter, Alcaligenes, Aerobacter, Azotobacter, Zeuglare*, various kinds of variants produced by variation of those bacteria by the known methods using NTG (nitrosoguanidine) and the like, and so on have been known.

Methods intended for improving the production efficiency of cellulose with *Acetobacter* strains have been proposed in a great number of patent applications including those filed by Biopolymer Research Co., Ltd. Methods of acquiring mutants and methods of using expensive and special agents are described in, for example, JP-A-62-265990, JP-A-63-202394, JP-A-63-74490, JP-A-2-238888, JP-B-6-43443, JP-B-5-1718, JP-A-7-184677 and JP-A-7-184675. Methods for controlling the conditions of the culture under agitation are disclosed in, for example, JP-A-9-94094 and the like.

In the known culture methods described above, a very small amount of water-soluble polysaccharide is produced at the same time, but almost all the cellulose material as a main product is recognized as a cellulose having β-1,4-glycoside linkages, and the ratio of Iα-crystals to Iβ crystals ((Iα/Iβ)×100, hereinafter referred to as Iα fraction), which is used in cellulose crystallography, is considered to be 64 to 72% (SCIENCE, Vol. 223, 283 (1984)). The Iα crystal essentially has a low surface activity, such as wettability, because when a specific crystal plane, particularly a (11-0) plane, is oriented, the hydroxyl group density in the crystal plane is lower than that of the Iβ crystal. Thus, a cellulose material produced by conventional microorganisms such as *Acetobacter* strains, in which the Iα fraction is as high as 64 to 72% and the (11-0) plane is oriented, essentially has a low surface activity.

Some patent publications disclose examples in which the cellulose conversion efficiency with respect to sugars that are used as carbon sources is 30% or greater in the production of the cellulose based material in the *Acetobacter* strains culture method. However, it can be considered that the cellulose conversion efficiency at a practical level is about twenty-odd %. These known culture methods are complicated in terms of their operation because a spinner culture acquires special features in view of the fact that *Acetobacter* strains which are aerobic bacteria are used.

Generally, spinner culture is used as an industrial production method, and the basic morphology of a produced cellulose material is disclosed in U.S. Pat. No. 5,144,021 (1992). According to the US patent, the cellulose material has a spherical or ellipsoidal shape with the size of about 0.1 to 10 mm as a macroscopic structure, the internal structure thereof is an interconnected network, and it is thus considered that the cellulose material has characteristics such that resistance to compression when wetted is high. However, high resistance to compression also means that it is hard for water to drain and thus drying is difficult. Furthermore, since fibrils extending radially do not exist around the above spherical or elliptic macroscopic structure, it can be considered that considerable energy is required for mutually and uniformly dispersing the macroscopic structures. Furthermore, according to U.S. Pat. No. 5,144,021, the degree of crystallinity is not so high, i.e. 70% or less, and it is thus conceivable that the strength of the cellulose itself and the performance when combined with other polymer material are poor.

A loosened material of bacteria cellulose having a sedimentation compression degree of 0.12 to 0.20 is disclosed in JP-B-2,877,676. Bacteria cellulose characterized in that the dynamic viscosity of an aqueous suspension of 0.1% bacteria cellulose is 1000 cp or greater (30° C., 10 rad/s) is disclosed in JP-B-2,971,024. These disclosures, like that of JP-B-6-43443, indicate that bacteria cellulose easily entraps water, and the conventional cellulose material has high thickening and dispersion effects, but has a disadvantage that considerable energy is consumed for processing the material into a solid product. On the other hand, bacterial cellulose produced by *Acetobacter* strains is used commercially only as acoustic oscillation plates.

Development of bacteria cellulose as food additives has been examined but has not resulted in actual commercialization. This is considered to be partly attributed to the fact that although the fibril produced by *Acetobacter* strains has remarkable characteristics of being as thin as several nm in diameter, its macroscopic morphology is simply an ellipsoid and is far from advantageous for processing as compared with other fibrous materials. Furthermore, as another reason, it is also considered to be attributed to the fact that bacterial cellulose has not been produced in a culture in a really functional manner.

The present inventors found through gene analysis of 16S-rRNA that microorganisms (CJF002 strain) highly homologous with *Enterobacter* produced a cellulose-like material, and filed a patent application for an invention of a method of applying the microorganisms to the tertiary recovery of petroleum (JP-A-2001-321164). In the patent application, static culture is described as a preferred culture method, and a method for blocking a water sweeping channel of a petroleum bedrock by the products of the microorganisms is disclosed, but the detailed structure, function and the like of various kinds of carbon sources relating to the produced cellulose-like material are not disclosed.

DISCLOSURE OF THE INVENTION

The present inventors found that a culture using cellulose-producing bacteria of *Enterobacter* could produce a new cellulose material. This new cellulose material has an almost spherical shape with the maximum diameter of several millimeters in which macrofibrils are formed radially from the center to the periphery, unlike the ellipsoidal morphology of the conventional microorganism-produced cellulose. This shape is easily separated from the culture broth, washed through a filter for purification and dispersed for formation into a secondary product. It can provide a bioprocess of low energy consumption, and has the possibility of exhibiting a new function derived from a specific shape different from that of the conventional material. Furthermore, the new cellulose material of the present invention has a very high degree of crystallinity and is therefore excellent in the strength of the cellulose itself and performance when combined with other polymer materials.

(1) The present invention relates to a spherical cellulose material wherein the cellulose material is a water-insoluble polysaccharide formed by β-1,4-type sugar chain linkages, the degree of crystallinity is 70% or greater, and macrofibrils are formed radially from the center to the periphery.

(2) Furthermore, the present invention relates to a cellulose material wherein the cellulose material is a water-insoluble polysaccharide formed by β-1,4-type sugar chain linkages, the composition ratio of glucose units in the water-insoluble polysaccharide is 85 to 100%, and an Iα fraction of a cellulose crystal polymorphism is not less than 45% and not more than 63%.

(3) Furthermore, the present invention relates to the cellulose material according to the above item (1) or (2), wherein the viscosity average polymerization degree determined by a viscosity method for cadoxene solution of cellulose is 3500 or greater.

(4) Furthermore, the present invention relates to the cellulose material according to any of the above items (1) to (3), which is obtained by culturing *Enterobacter* microorganisms, mutants thereof, or subculture microorganisms thereof.

(5) Furthermore, the present invention relates to the cellulose material according to the above item (4), wherein the above-described *Enterobacter* microorganism is of the CJF002 strain.

(6) Further, the present invention relates to a method for producing the cellulose material according to any of the above items (1) to (3), comprising inoculating a culture medium with at least one selected from the group consisting of *Enterobacter* microorganisms, mutants thereof and subculture microorganisms thereof in an amount of $10^3$ to $10^7$/ml and then culturing the microorganisms under agitation at a temperature of not less than 20° C. and not more than 45° C. using sugars as the carbon source.

(7) Further, the present invention relates to a composite of the cellulose material according to the above items (1) to (3) and other polymer material(s) and/or a metal and/or a metal oxide.

(8) Further, the present invention relates to a group of water-soluble polysaccharides having glucose, galactose and fucose as main components other than carboxylated sugars, which is obtained by inoculating a culture medium with at least one selected from the group consisting of *Enterobacter* microorganisms, mutants thereof and subculture microorganisms thereof in an amount of $10^3$ to $10^7$/ml and then culturing the microorganisms at a temperature of not less than 4° C. and not more than 30° C. using sugars as the carbon source.

BEST MODE FOR CARRYING OUT THE INVENTION

As a preferred aspect, a new material of the present invention is a cellulose material characterized in that the cellulose material is a water-insoluble polysaccharide formed by β-1,4 type sugar chain linkages, produced by *Enterobacter* microorganisms, for example CJF002 strain, mutants thereof or subculture microorganisms, the composition ratio of glucose units is 85 to 100%, the degree of crystallinity is 70% or greater, an Iα fraction that is used in the cellulose crystallography is kept at a low level as compared to the conventional bacteria cellulose produced by *Acetobacter* strains, and the morphology is that of a sphere in which macrofibrils are formed radially from the center to the periphery.

The cellulose material of the present invention may have in addition to β-1,4-type sugar chain linkages, 1,2-linkages, 1,3-linkages and 1,6-linkages. These linkages may be included in one molecular chain or present in a mixed state with water-insoluble polysaccharides other than cellulose (a polymer composed of a β-1,4-glucopyranose repeating chain) through hydrogen bonding and the like. Constituting sugars other than glucose are not specifically limited and include various kinds of hexoses, pentoses and carboxylated sugars, but are often galactose and mannose.

For the preferred water-insoluble cellulose material of the present invention, to describe in detail in terms of the structure, the Iα fraction is in a range of 45 to 63%, usually around 50%, which is smaller than that of cellulose produced by *Acetobacter* strains, i.e. 64 to 72%, and the degree of crystallinity is 70% or greater, particularly in some cases, greater than 90%.

Furthermore, the cellulose material of the present invention is composed of fibrils having a very small diameter of several tens of nm, and a sheet material prepared from the cellulose material has a very large number of entanglement points, and thus its mechanical strength is very high. A structure of cellulose produced by *Acetobacter* strains is described in U.S. Pat. No. 5,144,021, but according to the claims, its degree of cryatallinity is 70% or less, and therefore it is conceivable that its mechanical strength is lower than that of the cellulose material of the present invention. The degree of crystallinity described herein is a value determined from a solid-state $^{13}$C-NMR, and the details of its definition and measurement will be described below. The degree of crystallinity is generally determined by an X-ray diffraction, but in the case of cellulose produced of microorganisms conventionally and of the present invention, the measurement of the degree of crystallinity by X-ray diffraction is not suitable because a specific crystal plane is selectively oriented.

If a carbon source in culture is molasses, the composition ratio of glucose units is reduced but is not less than 85%. Furthermore, if the carbon source is sucrose or glucose alone, there are few cases that the composition ratio of glucose units is 100% and in most cases, it is about 98%.

Because the Iα fraction is low and galactose residues and mannose residues are introduced in the molecular chain, the cellulose material of the present invention has characteristics such as improved processability, alloy formation with other polymers, alloy formation with metals and metal oxides and adhesion to other materials as well as the ability to recognize or not recognize a protein, which could not be expected at all for the conventional bacteria cellulose whose characteristics such as transparence and mechanical strength have been utilized. Of course, this does not mean that the application of the cellulose material of the present invention to the conventional fields is not possible.

Furthermore, the cellulose material of the present invention has crystal components of cellulose II. The crystal surface of cellulose II has the crystal plane (11-0) on which hydroxyl groups selectively appear and the crystal plane (110) on which hydrogen atoms selectively appear, resulting in a crystal type essentially suitable for alloy formation.

The composition ratio of glucose units of the cellulose material of the present invention can be controlled by the ratio of sugar components used as a carbon source and culture conditions. In principle, if the number of types of sugars that are used as a carbon source is increased, constitutional sugar components of the obtained cellulose material are diversified. For increasing the amount of glucose components, glucose may be used for the carbon source.

Furthermore, the cellulose material of the present invention can be made to have almost the same degree of polymerization by application of synchronized culture. The degree of polymerization at the time of taking out the product is not specifically limited, but is preferably about 300 or more.

If the cellulose material of the present invention is required to have mechanical strength, it is preferable to adjust the degree of polymerization to 3500 or greater. However, the degree of polymerization described in the present invention is a value obtained by application of the cadoxene method to cellulose, and it is an approximate value particularly when the composition ratio of glucose is low.

The cellulose material of the present invention is characterized in that substantially spherical bodies with the maximum diameter of several millimeters which forms macrofibrils radially from the center to the periphery, exist independently or are linked together. The size of each spherical body and the form of each macrofibril can be controlled by the conditions of the culture under agitation.

For the culture under agitation, a rotation culture in which an agitation paddle is rotated, a shaking culture in which a container is reciprocated or rotated, and a culture under agitation by bubbling of air may be applied.

Figure 1:
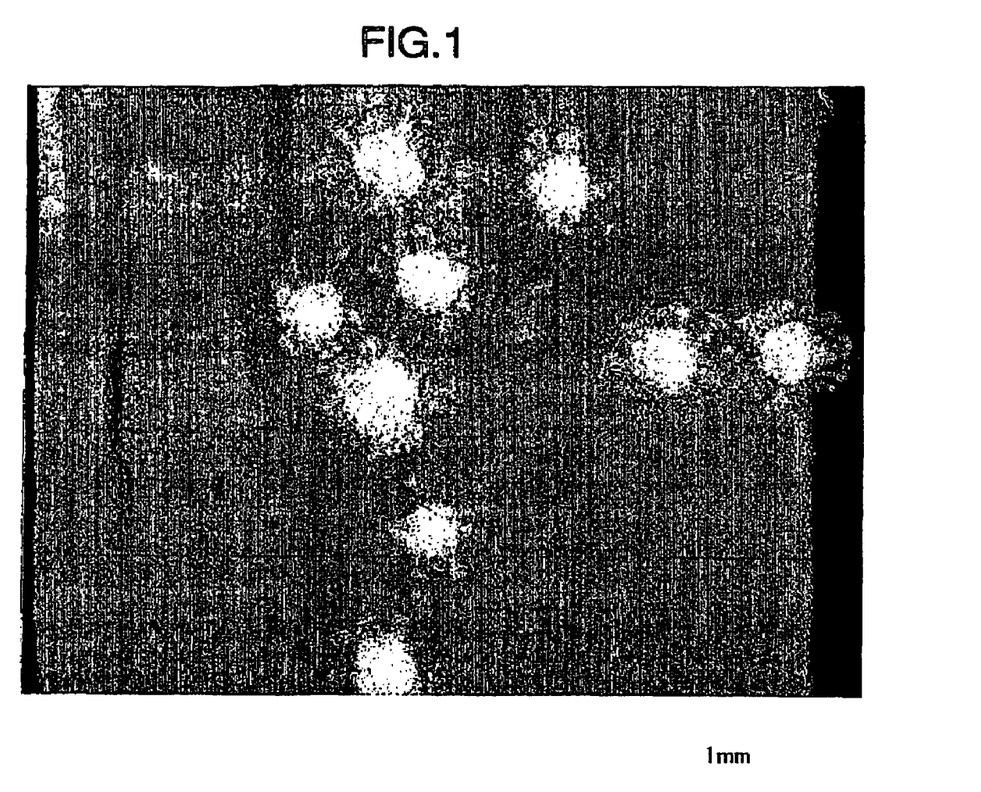
FIG. 1 is an optical microscope photograph (scale bar representing 1 mm) of a cellulose material of the present invention obtained by culture under agitation (stirring by rotator)
Figure 2:
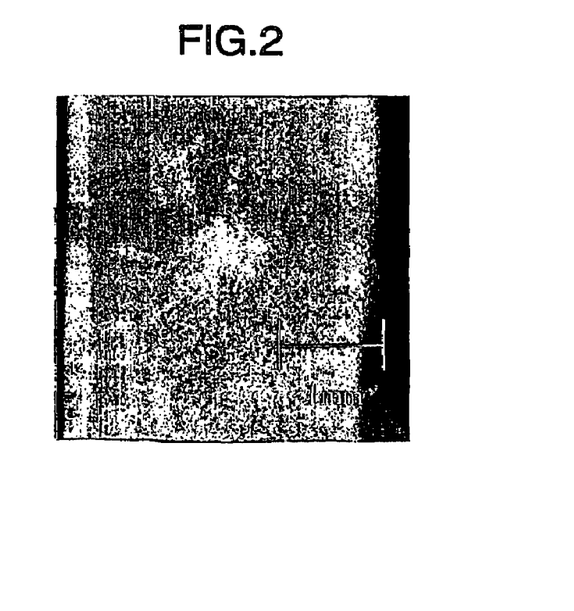
FIG. 2 is an optical microscope photograph (scale bar representing 1 mm) of a cellulose material of the present invention obtained by culture under agitation (air bubbling)

One example of the spherical body of the cellulose material of the present invention is constituted by spherical cores and conical components extending from the core radially, as shown in FIG. 1. The conical components and the core are jointed together at the tops of the conical components, and fibrous matter is observed at the bottoms of the conical components. The height of the conical components is almost equivalent to the radius of the core. This form is obtained by culture under agitation at a low speed. Conditions of the culture under agitation at low speed depend on the apparatus, particularly the size and shape of the agitation paddle, and cannot be defined unconditionally. If the agitation speed is too low, a problem arises such that the resultant cellulose material forms into an integral gel material and is entangled with the agitation paddle. If the agitation speed is too high, a strip-like cellulose material is obtained, the shape of which varies in the form of pulp, scale or the like with different sizes. As one example, when an agitation paddle having a diameter of 60 mm was used, a morphology shown in FIG. 1 was obtained with the rotational speed of 50 rpm to 200 rpm. Another example is shown in FIG. 2. The macrofibrils linearly extend in a length of about 1 mm radially from a spherical core having a diameter slightly smaller than 1 mm. This morphology was obtained by bubbling of air, and the amount of blown air is 1 $m^3$/minute of air per 1 $m^3$ of culture solution.

The size of the spherical core of the spherical body is 0.1 mm to several millimeters, but becomes very uniform as shown in FIG. 1 if production conditions are the same. The spherical body is easily separated through a rough mesh and easily purified. For example, the spherical body can be considerably dehydrated with simple compression, so that it may be processed into a product as it is (with more or less water included) or easily dried while being ablated. Depending on the final uses, protein removal operations may be unnecessary, resulting in considerable cost reduction. If protein removal operations are required, proteins may be removed by a treatment with protease, a surfactant or by oxidative bleaching. In some cases, a low-concentration aqueous alkaline solution may be used. Furthermore, the conventional cellulose produced by *Acetobacter* strains is a scaly strip-like and gel material and will therefore easily cause a mesh screen to be clogged, thus making it difficult to carry out the above-described step.

Microscopically, the spherical body is composed of microfibrils each with a size of 20 to 100 nm. Because the spherical body is composed of these microfibrils, the surface area of the spherical body is very large. The surface area measured by the nitrogen absorption method (BET method) is as large as approximately 50 to 150 $m^2$/g, which is about 100 times as large as the surface area of a general pulp. Because of the very large surface area, the spherical body of the cellulose material of the present invention is suitable for a carrier, an absorbent and the like, and can be directly filled in a column or the like utilizing its aegagropila-like form. The water-insoluble cellulose material of the present invention is significantly different in morphology from the conventional cellulose produced by *Acetobacter* strains which is essentially a gel, requires considerable energy for its ablation and drying and is valuable from an industrial viewpoint.

The diameter of the spherical body having the aegagropila-like form as the basic morphology can be empirically determined according to the initial concentration of inoculated bacteria, the size of a culture bath and the agitation speed.

The initial concentration of inoculated bacteria can be selected as appropriate and the appropriate concentration is about $10^3$ to $10^7$/ml. The pH of the culture medium is not specifically limited and is in a range of 2.2 to 9.5, preferably 5.0 to 8.0. The appropriate temperature is in a range of 20 to 45° C. In the process of cultural production of the cellulose material of the present invention, water-soluble polysaccharides of the present invention described below are produced at the same time, and maintaining the culture at a high temperature, e.g. 20° C. or higher, is preferable to improve the yield of the cellulose material.

Figure 3:
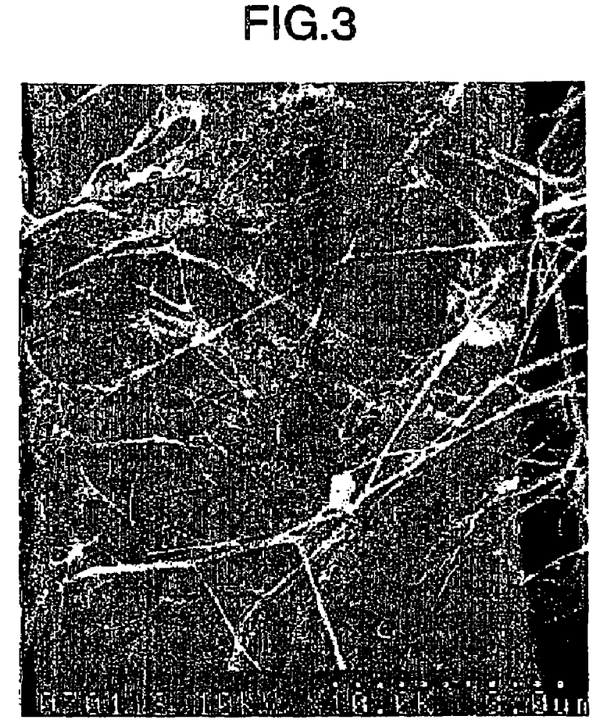
FIG. 3 is a scanning electron microscope photograph (scale bar representing 3 μm) of a cellulose material of the present invention.

The morphology of the spherical body at the microscopic level (as observed through an electron microscope) is a characteristic morphology in which a large number of flat microfibrils are highly entangled together, and circular pores in phase separation structure are mutually linked (FIG. 3). Here, the circular pore in phase separation refers to a flat pore structure formed in a poor solvent before polymer particles are capable of forming, i.e., when the polymer concentration is at a critical concentration or lower. When the polymer concentration is greater than the critical concentration in the poor solvent, primary particles of the polymer are generated to form a structure with the particles linked together. Bacteria cellulose described in U.S. Pat. No. 5,144,021 (1992) has a structure similar to the above structure with the primary particles linked together.

Owing to such a characteristic morphology, the purified cellulose material of the present invention is characterized in that the material has a very low slurry viscosity when it is redispersed in water and can be easily handled in secondary processing, unlike the so-called bacterial cellulose conventionally derived from *Acetobacter* strains. For example, the sedimentation compression degree of an aqueous dispersion (0.1 wt %) of bacteria cellulose derived from *Acetobacter* strains is 0.12 to 0.20, while that of the cellulose material of the present invention is as low as only less than 0.12. This means that wet compressibility is high. Therefore, for example, the cellulose material of the present invention is advantageous in the production of a very thin sheet and requires only a low energy for drying. The sedimentation compression degree herein is a ratio (B/A) of the sedimentation volume (B ml) of cellulose after centrifugation of a slurry at 1700 G for 30 minutes to the original volume of the slurry (A ml). Furthermore, the dynamic viscosity of a 0.1% aqueous suspension of an ablated material of bacteria cellulose derived from *Acetobacter* strains is 1000 cp or greater (30° C., 10 rad/S), while that of the cellulose material of the present invention is as low as only 200 cp. Owing to such characteristics, the cellulose material of the present invention can be very easily processed into various kinds of sheets and separators. These characteristics are considered to result mainly from its characteristic morphology but they may be associated with the orientation of OH groups on the surfaces of microfibrils and the small I$\alpha$ fraction of 50 to 60%.

The novel cellulose material of the present invention is suitable as a material for forming a composite with a polymer material other than cellulose or an inorganic substance such as a metal or metal oxide.

Polymers for use in the formation of composites include, but are not limited to, for example, general hydrophobic polymers such as polyethylenes (PE), polypropylenes (PP) and polystyrenes (PS), hydrophilic polymers such as polyalkylene oxides (PAO), and super engineering plastics such as polysulfones (PSu), polyamides (PA), polyesters (PET) and polyimides (PI). Alloys with these polymers may be prepared. Particularly, the cellulose material of the present invention is adjusted to have an I$\alpha$ fraction lower than that of cellulose derived from *Acetobacter* strains, resulting in an improvement in balance of orientation of OH groups of the cellulose material, and it is easily combined with various kinds of polymers in principle. Galactose is said to selectively recognize proteins and the like, and the existence of galactose as a constitutional sugar makes combination with proteins and the like easier. Thus, the cellulose material is relatively easily combined with various kinds of polymers under the presence of a small amount of a hydrophilic solvent and/or a hydrophobic solvent and can be developed as useful functional materials or industrial materials. Of course, protein derived from the bacteria used in the present invention can be utilized as a material to be combined, thus contributing to cost reduction for materials and methods for combination along with effective utilization of a culture system. Furthermore, the cellulose material of the present invention has microfibrils with a size of about 50 nm as constitutional units and therefore, the formation of a composite at the nanolevel is possible.

Examples of inorganic substances such as metals and metal oxides for use in forming a composite with the cellulose material of the present invention, water-soluble polysaccharides or these mixtures, include gold, silver, copper, platinum, palladium, aluminum, iron, bismuth and magnesium or alloys thereof and oxides thereof, which are magnetic materials, dielectric materials, reaction catalysts and the like. Methods for forming a composite may include, but are not specifically limited to, a method using high acceleration ball mills, a method using a Banbury mixer, a repetitive rolling method of carrying out high-pressure pressing repeatedly many times, and a wet dispersion method of forming a composite in a polymer solution.

As a suitable method for forming a composite, an inorganic substance is originally dispersed in such a culture solution, or the inorganic substance is added to the culture solution at some point in time after starting the culture, whereby a novel microorganism-produced cellulose/inorganic substance composite essentially maintaining the morphology of the present invention is produced. Examples of inorganic substances that are suitably used include inorganic oxides or hydroxides capable of forming a colloid at a charge zero point of 7 or greater in pH, for example $\alpha$-alumina, $\gamma$-alumina, boehmite, bayerite, beryllium oxide, cadmium oxide, cadmium hydroxide, cobalt hydroxide, copper oxide, iron hydroxide, $\alpha$-iron oxide, $\gamma$-iron oxide, lepidocrocite, lead hydroxide, magnesium oxide, magnesium hydroxide, manganese hydroxide, thallium oxide, vanadium oxide, zinc oxide and lanthanum oxide. Furthermore, as other examples, inorganic oxides or hydroxides capable of forming a colloid at a charge zero point of 7 or less in pH, for example aluminum compounds such as diaspore and gibbsite, iron hydroxides such as getite, silicon oxide, tin oxide, titanium oxide, zirconium oxide, titanates other than alkali metal salts, zirconates other than alkali metal salts and the like are suitably used. Since they hardly increase the viscosity of the culture medium, the amount and the particle size when they are added to the culture medium are not limited and may be determined as appropriate in terms of the culture technique by one skilled in the art. However, if the amount or size is large and uniform dispersive mixing with the cellulose material being produced is desired, the air permeability and agitation should be enhanced. These composites can allow the function specific to the inorganic substances to be exhibited effectively. If these inorganic materials are mixed with the cellulose material in the form of composites, they have an effect of facilitating micro dispersion and can impact their reinforcement function to the cellulose material. For example, composites with aluminum oxide may be used as raw materials of abrasive materials, catalyst carriers, gas cleaning filters, liquid cleaning filters, separation films, absorption and separation materials for organic solvents, in particular organic chlorine-based solvents, ink absorption materials, humidity controlling materials and the like. Composites with titanium oxide may be used as UV absorbers and photocatalyst materials. Composites with barium carbonate may be used as raw materials of X-ray shields and ferroelectric materials. Composites with zirconium oxide may be used as raw materials of low heat conductive materials and highly refractive materials. Composites with cobalt oxides may be used as raw materials of paramagnetic/low electrically conductive materials. Composites with barium titanate may be used as raw materials of ferroelectric materials. Composites with $\gamma$ ferrite may be used as raw materials of ferroelectric materials. Furthermore, composites with zinc oxide may be used as raw materials of catalysts, bases of photosensitive materials and raw materials of rubber curing reinforcing materials.

The cellulose material/inorganic substance composites obtained in the culture process according to the present invention is separated from the culture medium in the form of the composites and can be used as final raw materials in the original composite state even in the final stage. Therefore, the cost for disposing of waste liquid per unit quantity of products is considerably reduced.

These composites can more effectively exhibit the function of an inorganic oxide to be added. For example, composites with α-alumina, γ-alumina, cobalt hydroxide, vanadium oxide and the like can be used as various kinds of catalyst carriers for use in an aqueous medium and nano-dispersion abrasive base materials; composites with zinc oxide can be used as electroluminescence dispersion base materials; composites with titanium oxide can be used as photocatalyst base materials; and composites with barium titanate can be used as highly dielectric base materials.

The cellulose material of the present invention has various characteristics such as a fine microfibril structure with a size of 50 to 100 nm, an extremely large specific surface area, excellent protein absorptivity, a small linear expansion coefficient and a high elastic efficient, and therefore can be used for various applications in addition to alloy formation described herein. As applications, for example, it can be developed as non-woven fabrics, absorbents, protein absorbents because of especially strong interaction with proteins, separation membranes, artificial skins, carriers, water retention agents, thickening agents, dispersion/suspension stabilizers, food materials and the like. It may also be used for microporous membranes, foams, rubbers, latexes, adhesives and the like as constitutional components of composite materials. For these applications, the conventional cellulose produced by Acetobacter strains can be utilized to some extent. However, it is apparent that the cellulose material according to the present invention strongly interacts with other materials and is thus more effective in the above described applications than the conventional cellulose, because it has a low Iα fraction, hence a high density of OH groups on the surface and a high surface activity and contains galactose residues and mannose residues.

A method for producing the cellulose material of the present invention will be described below.

Cellulose-producing bacteria belonging to the *Enterobacter* genus may be used as cellulose material producing bacteria for use in the present invention. For example, CJF002 strain, subculture microorganisms thereof, various kinds of mutants produced by mutating those microorganisms by the well-known methods using NTG (nitrosoguanidine) or the like, and so on may be used. Here, the CJF002 strain refers to an *Enterobacter* microorganism strain deposited as "*Enterobacter* sp. CJF-002" in National Institute of Advanced Industrial Science and Technology, International Patent Organism Depositary (IPOD) located at Central 6, 1-1-1, Higashi, Tsukuba, Ibaraki, Japan, as the original deposition, on Mar. 29, 2000, and transferred from the original deposition to a deposition under Budapest Treaty as Accession No. "FERM BP-8227" on Nov. 1, 2002.

There is an advantage that bacteria capable of producing the cellulose material of the present invention are facultative anaerobic bacteria and thus can be cultured irrespective of the presence or absence of oxygen (air). For the culture medium, various kinds of synthetic and natural culture media may be used. Culture media containing sugars are preferable. Carbon sources include glucose, fructose, galactose, maltose, sucrose, levan, mannitol, sorbitol, erythritol, glycerin, ethylene glycol, starch, syrup, corn/stape/liquor, malt extracts and starch hydrolysates. In the case of CJF002 strain particularly, various kinds of organic acids of fruit juices such as citrus molasses, beet molasses, cane molasses, beet juices, sugarcane juices and citruses as the so-called molasses that are inexpensive but cannot be utilized for the conventional *Acetobacter* strains, may be used alone or in a mixture of two or more. For the nitrogen source, inorganic nitrogen sources such as ammonium salts and nitrates and organic nitrogen sources such as fermentation media, peptones, soybean powders, meat extracts, caseins, urea and soybean milks may be used alone or in mixture of two or more.

For the culture medium, amino acids, vitamins and fatty acids as organic trace nutrients or phosphates, iron salts, manganese salts and other metal salts as inorganic salts may be used alone or in mixture of two or more types as appropriate.

Since *Enterobacter* microorganisms for use in the present invention, for example CJF002 strain microorganisms, mutants thereof or subculture microorganisms are facultative anaerobic bacteria, the culture proceeds irrespective of aerobic or anaerobic conditions to produce a group of cellulose materials of the present invention. The culture form is not limited and in principle, a well known method for use in the culture of microorganisms may be used to carry out the culture. For example, means and apparatuses such as agitation tanks, which include, for example a jar fermenter and a tank, a flask with a baffle, a Sakaguchi flask and an air lift type agitation tank, pump drive circulation of fermentation broth and shaking culture in which a container itself is reciprocated and rotated, may be arbitrarily selected, combined and used. Furthermore, culture under agitation may be carried out while blowing gas at the same time as required. For blowing gas, for example, oxygen-containing gas such as air, or for example, oxygen-free gas such as argon or nitrogen may be used. Such gas can be selected as appropriate by one skilled in the art depending on conditions of the culture system.

Furthermore, in the culture process, the well known process, for example, batch fermentation process, repetitive batch fermentation process, continuous fermentation process or the like may be used. In the present invention, an especially preferable culture method is aerobic culture under agitation. In static culture, the cellulose material of the present invention is usually produced in a gel form, and thus the purification and ablation thereof are difficult. However, special stress should be laid on the advantage that in the production of the cellulose material by CJF002 strain microorganisms, mutants thereof or subculture microorganisms, the probability that bacteria are buried in the produced gel is low unlike *Acetobacter* strains and therefore the purification is relatively easier as compared to production by *Acetobacter* strains.

The special characteristics provide an advantage when the culture under agitation is performed at a low speed. A very specific independent release material (aegagropila-like form) shown in the photograph of FIG. 1 can be generated. This is highly advantageous, since the bacteria can be removed by rinsing alone, resulting in a significant reduction in cost depending on the final use.

In actual cultures, the initial concentration of bacteria can be selected as appropriate, but the appropriate concentration is about $10^3$ to $10^6$/ml, preferably about $10^3$ to $10^6$/ml. The pH of the culture medium is not limited, but is preberaly 2.2 to 9.5, and more preferably around 7. The appropriate temperature is in a range of 20 to 45° C. In the present invention, if the CJF002 strain is used, in particular, a group of water-soluble polysaccharides are formed at the same time in the process of the culture production of the cellulose material, and maintaining the culture at a high temperature, for example at 30° C. or higher is preferable for improvement of the yield of the cellulose material.

Another novel material according to the present invention is a group of water-soluble polysaccharides having glucose, galactose and fucose as main components other than a carboxylated sugar, which are each contained in a content of around 30%. Production of such a group of water-soluble polysaccharides is one of characteristics in the culture of a group of microorganisms for use in the present invention. For example, by simply reducing the culture temperature to about 30° C. or lower, a group of water-soluble polysaccharides can be produced as the main product. The reason why the term "a group of water-soluble polysaccharides" is used is that it can be further separated into several kinds of water-soluble polysaccharides if more precise solubility separation is carried out. Practically, however, since fine separation may be unnecessary, and there are many cases where use of these polysaccharides in a mixed state is more advantageous in terms of cost reduction, the material is consciously described as a group of water-soluble polysaccharides. The term "water-soluble" includes materials exhibiting high swelling properties.

The case in which a deoxy derivative with the C6 position substituted with methyl such as fucose is incorporated in the chain, like the (group of) water-soluble polysaccharides of the present invention, is unique. If the water-soluble polysaccharides are cross-linked with a general cross-linking agent, they become a gel with water, etc. highly absorbed thereby and are easily used in a biocompatible material, a medium for a drug delivery system (DDS) and an agent capable/incapable of recognizing cells if they are applied to the surface of another material or is incorporated in another material and then molded. Furthermore, the group of water-soluble polysaccharides of the present invention has an excellent ability to disperse different materials and has a strong dispersion holding power in the presence of a salt, which is the problem that cellulose-based dispersants always encounter. Thus, the group of water-soluble polysaccharides can be used for a wide range of industrial applications including cosmetics. Of course, it can basically form an alloy with other materials, e.g. a polymer material, as described with the water-insoluble cellulose material.

The group of water-soluble polysaccharides of the present invention may be produced in a culture medium that is essentially the same as that of culture production of the cellulose material described previously, but it is produced as the main product if the culture is carried out at a low culture temperature, e.g. a temperature lower than 20° C. For the carbon source, sucrose is more preferable than glucose. In this case, the cellulose material is more or less produced. The production ratio of the group of water-soluble polysaccharides to the cellulose material increases at a low temperature, but either product is hardly produced at a temperature lower than 4° C. Since enormous energy and cost are required for separation/generation of a group of polysaccharides dissolved in the culture medium, it is necessary that the group of polysaccharides should exist in a high concentration in the culture medium.

For the method for purifying from the culture broth, the cellulose material, the composite and the group of water-soluble polysaccharides obtained by the method of the present invention, various methods may be applied, without limitation, such as cleaning by filtration and decantation by centrifugal sedimentation. The degree of purification may be selected as appropriate according to the application, and proteins derived from microorganisms, culture medium components and the like may exist depending on the application. In some cases, the existence of proteins derived from microorganisms may bring about a more effective result for the purpose of improving the adhesion to other components or other purposes. The cellulose material and the group of water-soluble polysaccharides may be mixed.

The present invention will now be described further specifically by way of Examples. Furthermore, methods for identification and evaluation of the cellulose material and the like produced by the culture method of the present invention will be described below.

(1) Analysis of Sugar Components of Freeze-Dried Products of Cellulose Material and Group of Water-Soluble Polysaccharides A freeze-dried product of a cellulose material was hydrolyzed with a commercially available cellulase (degree of hydrolysis: about 75%). Also, a freeze-dried product of a group of water-soluble polysaccharides was decomposed with an inorganic acid, and the residues were further hydrolyzed with cellulose. The resultant decomposed material was analyzed for neutral sugars and uronic acid according to the conditions described below.

(i) Neutral Sugars

Using a HPLC apparatus (LC-9A) manufactured by Shimadzu Corp. and a column (TSK-gel Sugar AXG: φ4.6 mm×150 mm)) manufactured by Tosoh Corporation, a sample was injected and then eluted at 0.4 ml/min using a 0.5 mM potassium borate buffer solution as an elute. As a post column label, 1% arginine and 3% boric acid were used. The flow rate was 0.5 ml/min and the reaction temperature was 150° C.

(ii) Uronic Acid

Analysis was carried out in the same manner as in the analysis of neutral sugars, except that a column (Shinpal ISA-07: φ44.6 mm×250 mm) manufactured by Shimadzu Corp., and the flow rates of the elute and the post column label were each changed to 0.8 ml/min.

(2) Linkage Form of Constitutional Sugars of Cellulose Material

A freeze-dried product of a cellulose material was fully methylated according to the conventional method, hydrolyzed into monosaccharide units with trifluoroacetic acid and then reduction-acetylated by the acetic anhydride-pyridine method to convert into an acetyl derivative of a partially methylated sugar alcohol (partially methylated alditol acetate). The linkage form of the cellulose material was estimated from methylation analysis using gas chromatography (HP 5890A manufactured by Hewlett-Packard, SPB-5 column manufactured by Supelco Japan Ltd., carrier gas: He, detection mode: FID) and gas chromatography-mass spectroscopy analysis (JMS DX-303 manufactured by JEOL Ltd., ionization; EI method).

(3) Iα Fraction of Cellulose Material

Figure 6:
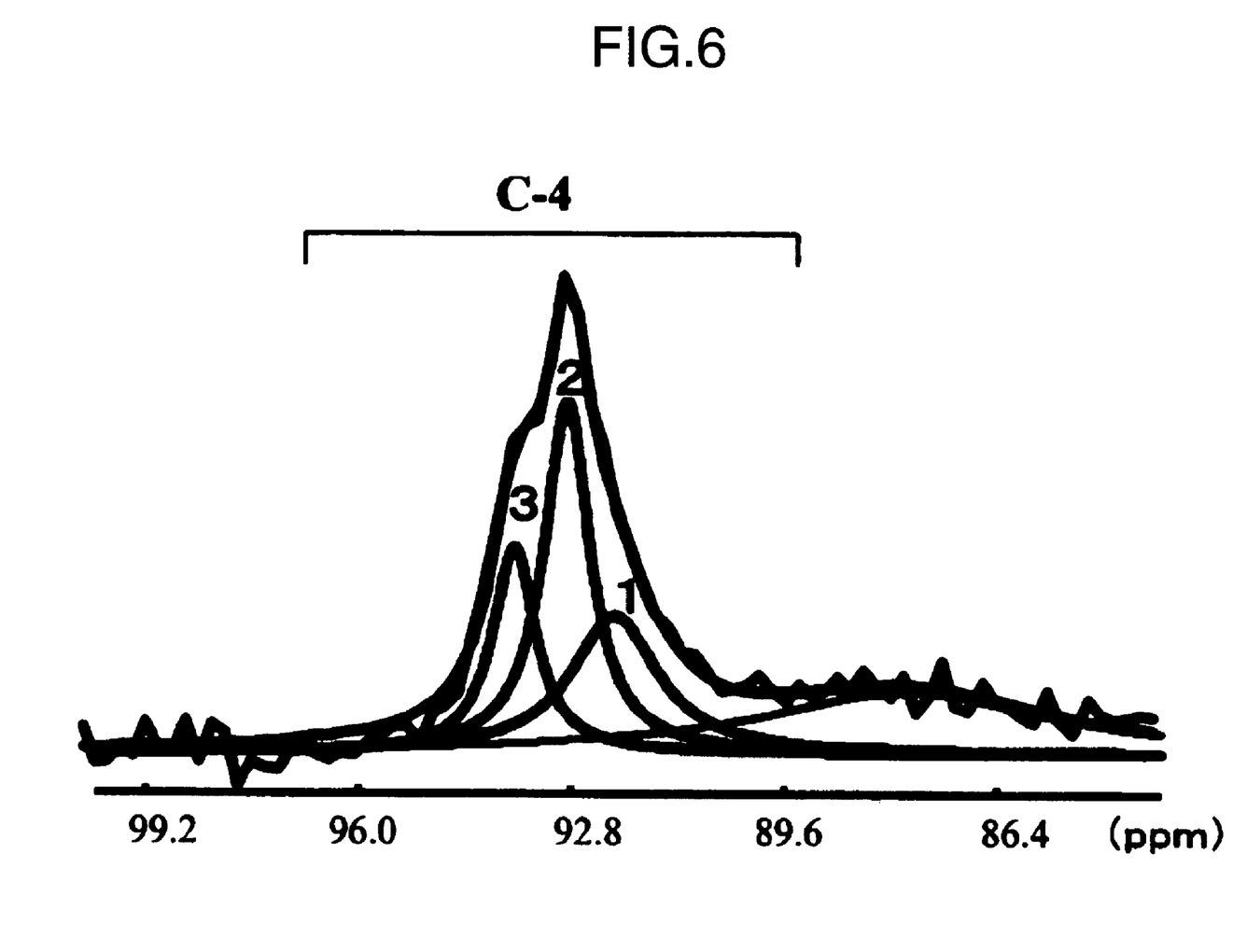
FIG. 6 shows a solid-state 13C-NMR spectra of cellulose materials of the present invention.

A solid-state $^{13}$C-NMR spectrum measurements was made using DSX 400 Spectrometer manufactured by Bruker Co., Ltd. and the CP/MAS method. The contact time was 1 ms, the pulse interval 5 s, the 90° pulse 4.8 μs, the number of accumulations 3000 and the rotation speed 4000 Hz. The Iα fraction was calculated from the resultant solid-state $^{13}$C-NMR spectra (FIG. 6) and the following equation (see Macromolecules, 17, 1465 (1984)). FIG. 6 shows the solid-state $^{13}$C-NMR spectra of the cellulose material of Example 1 obtained with glucose as a carbon source. This spectra show carbon at the C4-carbon of a glucose unit being a constitutional sugar unit of the cellulose material. Iα components appear at peak 2 (Iα/2+Iβ/2) and peak 3 (Iα/2) and the contribution ratios of Iα components are each 0.5 as shown in parentheses. Iβ components appear at peak 1 (Iβ/2) and peak 2 (Iα/2+Iβ/2) and the contribution ratios of Iβ components are each 0.5 as shown in parentheses. Thus, the Iα fraction can be determined from the following equation:

$$I\alpha \text{ fraction} = (I3 \times 2/(I1+I2+I3)) \times 100$$

I1: integrated intensity of peak 1, I2: integrated intensity of peak 2, I3: integrated intensity of peak 3.

(4) Orientation of Crystal Plane for Cellulose Material

Figure 7:
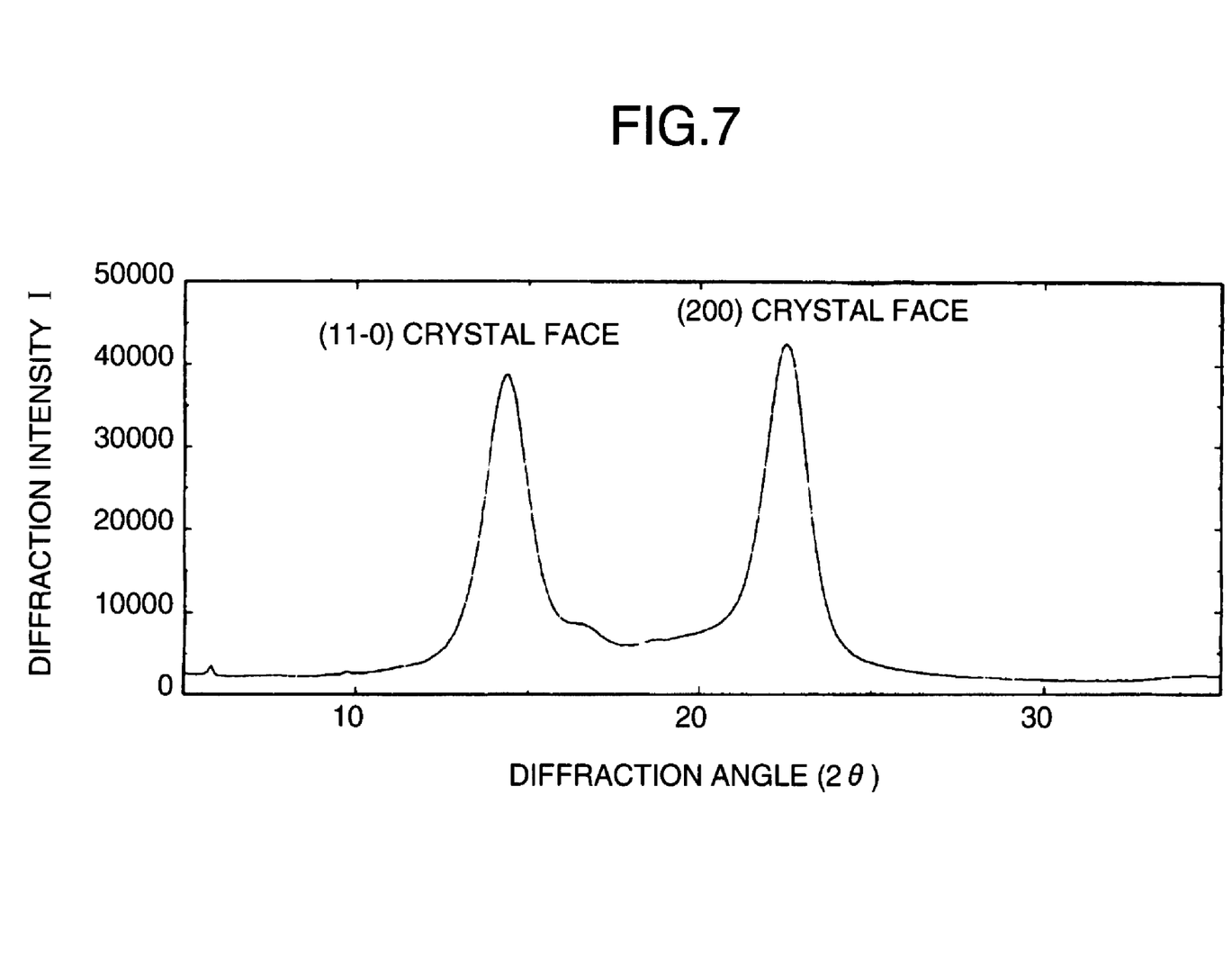
FIG. 7 shows a wide angle X-ray diffraction spectrum of a cellulose material of the present invention.

Plane orientation was calculated from the results of a wide angle X-ray diffraction (FIG. 7) and the following equation (Polymer Journal, 7, 157 (1975)):

$$\text{Plane orientation} = (I11\text{-}0/I200) \times 100$$

I11-0: diffraction intensity of (11-0) crystal plane, I200: diffraction intensity of (200) crystal plane.

(5) Polymerization Degree of Cellulose Material

Molecular weight M was calculated from an intrinsic viscosity ($\eta$) obtained by a viscosity method for the cadoxene solution and the following equation (see European Polymer Journal, 1, 1 (1965)), which was then divided by 165 to determine a degree of polymerization. FIG. 7 shows a wide angle X-ray diffraction pattern of the cellulose material of Example 1 obtained using glucose as a carbon source.

$$[\eta] = 3.85 \times 10^{-2} M^{0.76}$$

(6) Degree of Crystallinity

A solid-state $^{13}$C-NMR spectrum was measured by the CP/MAS method by using DSX 400 Spectrometer manufactured by Bruker Co., Ltd. The contact time was 1 ms, the pulse interval 5 s, the 90° pulse 4.8 μs, and the number of accumulations 3000 and the rotation speed 4000 Hz. In the C4-carbon peaks of the resultant solid $^{13}$C-NMR spectrum, the peak on the high field side was defined as an amorphous component (peak area A) while the peak on the low field side was defined as a crystal component (peak area B). Degree of crystallinity $\chi c$ was determined from the following equation (see Polymer Journal, 17, 707 (1985) (K. kamide, K. Okajima, K. Kowsaka, T. Matsui):

$$\chi c = (B/(A+b)) \times 100$$

EXAMPLE 1

A polysaccharide production medium (hereinafter referred to as PPM medium. Polysaccharide-production-medium, Akihiko Shimada, Viva Origino, 23, 1, 52-53, 1995) containing 4.0% sucrose, glucose or China-made beet molasses was subjected to high pressure steam sterilization processing. Then, 1000 ml of the medium was put in a jar fermenter with the inner volume of 2000 ml, inoculated with the CJF 002 strain in an amount of 10$^4$ CFU/ml and cultured under agitation at a low speed (70 rpm) at 30° C. for 2 days under gentle bubbling aeration. In all types of cultures, a cellulose material of spherical form having macrofibrils formed radially from the center to the periphery as shown in FIG. 1 was obtained. Specifically, it was composed of a spherical core and conical components extending radially from the core. The conical components and the nucleus were jointed together at the top of the conical components, and fibrous matter was observed at the bottom of the conical components. The height of the conical components was almost equivalent to the radius of the spherical cores. They were filtered with a screen mesh (50 mesh), rinsed, compressed, then immerged in a 1% NaOH solution, sterilized, neutralized again, rinsed and compressed, whereby a white floccular body containing water could be easily obtained. The cellulose material obtained by culture with glucose had a shape shown in FIG. 1 and was generally uniform in diameter, and was excellent in liquid permeability. The above-described steps of filtration, rinsing, compression and so on were very satisfactory. As described below, the conventional cellulose by Acetobacter strains is a scaly strip and gel material and therefore causes screens to easily be clogged, thus making it difficult to carry out the above-described steps. It was found that almost all bacteria were eliminated by rinsing alone without immersion in the 1% NaOH solution.

The results of analysis of constitutional sugar components, the degree of crystallinity, analysis of the Iα fraction and analysis of the orientation of crystal plane are shown in Table 1. Apparently, β-1,4-linkages predominated, the glucose content of the constitutional sugars was 87.8 to 99.6%, the degree of crystallinity was 80% or greater, and the Iα fraction was 62% at most and 57% on average. The fact that the Iα fraction was lower than that of cellulose produced by Acetobacter strains in Comparative Example 2 described below is attributable to the coexistence of water-insoluble polysaccharides having a structure close to that of the real cellulose structure composed of only glucose. Sugar components other than glucose were mainly galactose and mannose. The yield of the water-insoluble cellulose material based on sugars was 10 to 15%.

EXAMPLE 2

One cubic meter (1 m$^3$) of a polysaccharide production medium (Polysaccharide-production-medium, Akihiko Shimada, Viva Origini, Vol. 23, No. 1, pp. 52-53, 1995) containing 2.0% glucose subjected to high pressure steam sterilization processing was put in a 3 m$^3$ culture tank, inoculated with the CJF 002 strain in an amount of 2×10$^4$ CFU/ml, bubbled from the bottom of the culture tank at an aeration rate of 1 m$^3$/minute, and cultured at 30° C. for 24 hours. An adjustment was made with a dilute NaOH solution at intervals of one hour so that the pH in the culture was 7. After the culture was completed, the medium was sterilized by blowing high pressure steam thereto, filtered with a coarse mesh, subjected to centrifugal dehydration processing, then subjected to bacteriolysis with 1% caustic soda at 90° C. for several hours, neutralized, rinsed and dehydrated to obtain a wet cake containing about 10 Wt % of cellulose. The cake was directly diluted with water, and its macroscopic structure was observed with an optical microscope. The result is shown in Table 2. FIG. 2 shows a spherical form that is essentially same as that of FIG. 1 in which macrofibrils are formed radially from the center to the periphery, but they are different in shape and size of the fibril because the culture conditions are different. Specifically, the macrofibrils linearly extend in a length of about 1 mm radially from a spherical core having a diameter slightly smaller than 1 mm. As compared to the scaly strip or indeterminate form of bacteria cellulose obtained by culture under agitation of Acetobacter strains (K. Watanabe, Cellulose 5, 187 (1998)), the microorganism-produced cellulose of the present invention has an independent or somewhat linked unique structure in which the macrofibrils extend radially from the center and is thus an utterly novel microorganism-produced cellulose material.

Furthermore, the microscopic structure of a sample obtained by freeze-drying the above wet cake was observed with an electron microscope. The result is shown in FIG. 3. Bacteria cellulose obtained by culturing Acetobacter strains under agitation is reticular, but its microfibrils themselves are rounded and have a structure close to the structure in which transient particles of a produced polymer are linked by phase separation (see U.S. Pat. No. 5,144,021, FIG. 2). On the other hand, as shown FIG. 3, the product of the present invention is generally flat and has a characteristic morphology in which circular pores are mutually linked as in the phase separation structure and has a much higher degree of mutual linkage among microfibrils. Furthermore, the linkage form of constitutional sugars of the cellulose material of the present invention was analyzed and as a result, it was found that β-1,4-glycoside linkages represented 96% or more of total linkages, and cellulose predominated in the constitutional sugars. Furthermore, the degree of crystallinity was 90% or greater, and it was found from X-ray diffraction that the II-type crystal form more or less existed.

EXAMPLE 3

Figure 4:
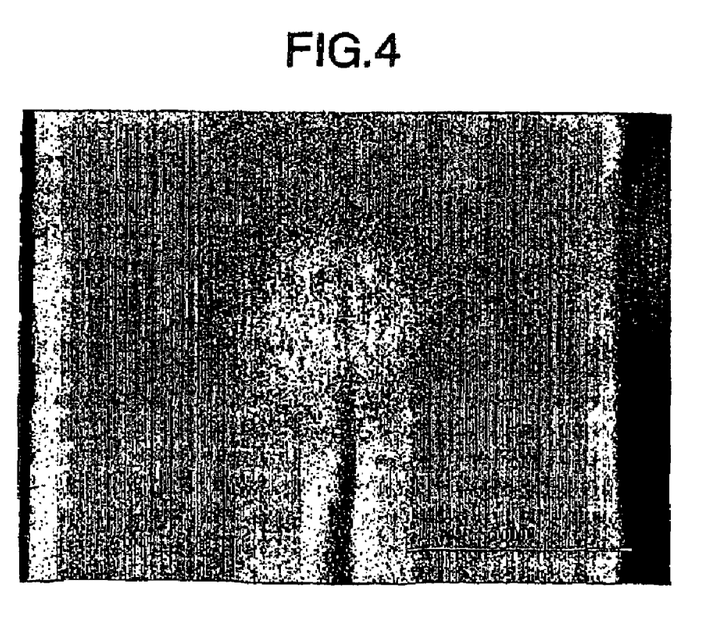
FIG. 4 is an optical microscope photograph (scale bar representing 5 mm) of a composite of the cellulose material/inorganic material of the present invention obtained by culture under agitation with alumina added.
Figure 5:
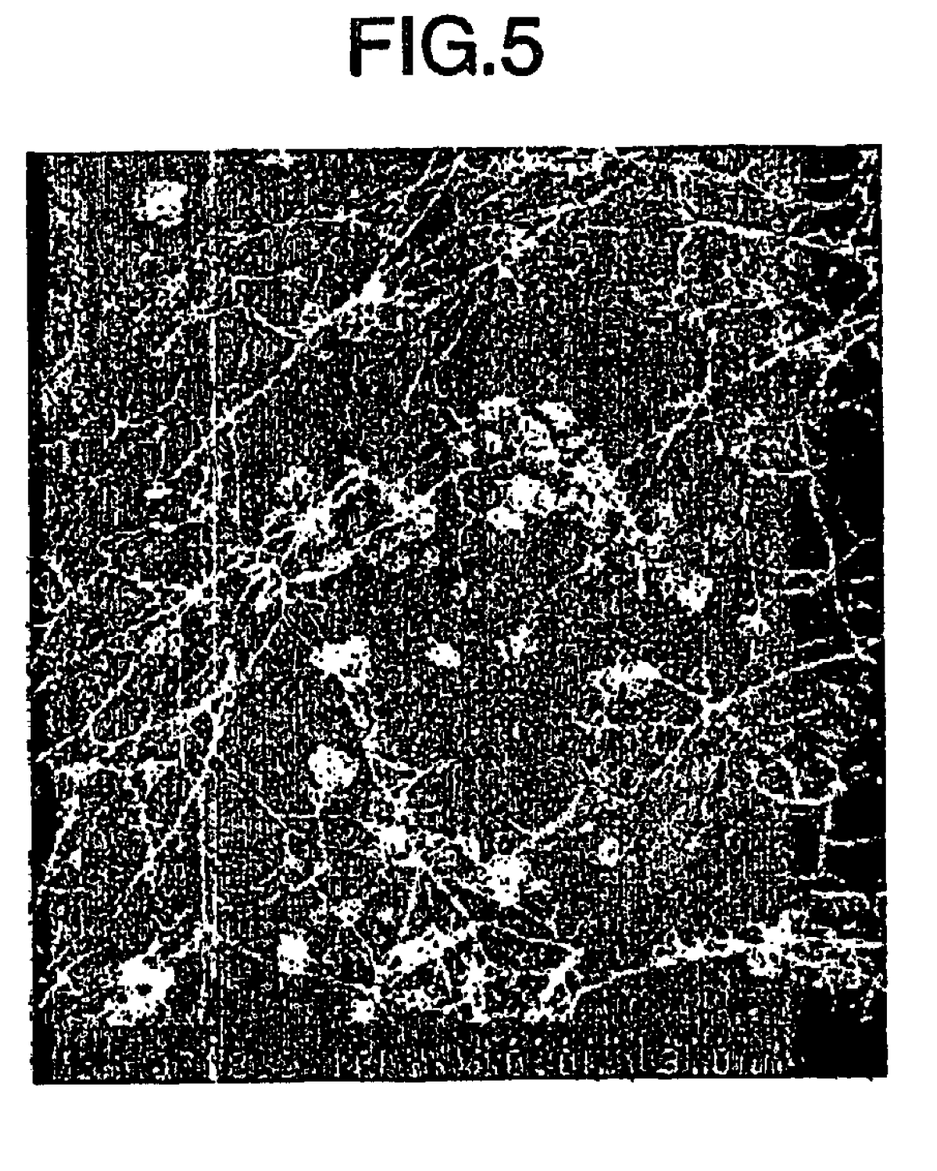
FIG. 5 is a scanning electron microscope photograph (scale bar representing 3 μm) of a composite of the cellulose material/inorganic material of the present invention obtained by culture under agitation with alumina added.

One thousand milliliters of PMM with a glucose concentration of 3% was put in a small jar fermenter having a total volume of 5000 ml, then sterilely inoculated with the CJF002 strain ($2\times10^4$ CFU/ml), and to which α-alumina (average particle size of 0.5 μm, 300 mg) was added, and cultured under agitation at an agitation rotation speed of 100 rpm and at an aeration rate of 600 ml/min for 48 hours. The medium was sterilized, dehydrated, washed by an alkali, neutralized, washed and dehydrated to obtain a cellulose material/inorganic substance composite. An optical microscope photograph thereof is shown in FIG. 4. For the composite with alumina added, the similar morphology, i.e. a novel morphology having radial macrofibrils around a large spherical core was clearly observed. The spherical body has a size twice or more as large as that of the spherical body where no alumina exists. In this Example, if alumina is fully incorporated in the produced cellulose material, the content of alumina is about ⅟25 as a volume fraction. An electron microscope photograph of a freeze-dried product of the cellulose material/inorganic substance composite is shown in FIG. 5. It was found that alumina of indeterminate form is fixed on areas of a highly spidery structure. This freeze-dried product was subjected to redispersion processing several times and observed again by an electron microscope. As a result, it was found that the fixed alumina was hardly separated or detached from the cellulose microfibrils.

EXAMPLE 4, 5 AND 6

Five grams of α-alumina (Example 4) (average particle size of 0.5 μm), 5 g of anatase-type titanium oxide (Example 5) (particle size of 0.5 μm) and 5 g of rutile-type titanium oxide (Example 6) (particle size of 0.5 μm) were separately mixed and each was dispersed in 500 ml of PMM with a glucose concentration of 2%, and put sterilely in each flask having a total volume of 2000 ml, inoculated with the CJF002 strain ($2\times10^4$ CFU/ml). A shaking culture was conducted at a shaking speed of 200 rpm for 18 hours. Aeration and pH adjustment were not conducted. Immediately after the sterilization, the amount of consumed glucose was measured to find that there was a large difference in the amount of consumed glucose with 94% for α-alumina, 36% for anatase-type titanium oxide and 21% for rutile-type titanium oxide. It may be ascribable to the fact that the surfaces of the latter two materials are alkaline and the surface of the former material is acidic. The resultant cellulose material/inorganic substance composite was observed with an optical microscope and as a result, in each Example, a spherical form with macrofibrils formed radially from the center to the periphery was observed. In the case of titanium oxides where glucose was less consumed, the amount of cellulose was almost equivalent to that in the case of alumina. Thus, the efficiency of conversion from glucose into cellulose seems to be improved.

EXAMPLE 7 AND COMPARATIVE EXAMPLE 1

The wet cake of the novel microorganism-produced cellulose material obtained in Example 2 was diluted with water so that the cellulose content was 0.1 Wt %, and dispersed in a simple manner with a TK homogenizer to obtain a dispersion (Example 7). Commercially available Nata de coco (bacterial cellulose pericle obtained by static culture with *Acetobacter* strains) manufactured by Fujicco Co., Ltd. was similarly dispersed in a simple manner with the TK homogenizer to obtain a 0.1 wt % cellulose dispersion (Comparative Example 1). The sedimentation compression degrees of these dispersions were measured by the method described in this specification. As a result, it was found that the sedimentation compression degree was 0.20 or greater in Comparative Example 1, while it was 0.08 for the product of the present invention Example 7. This means that the latter is more easily compressed. Similarly, the dynamic viscosity was measured at a rotation speed of 10/SEC using a B-type viscometer. The product of the present invention had a dynamic viscosity of 200 cp, while the product of Comparative Example 1 had a dynamic viscosity of 600 cp. That is, it can be said that the novel microorganism-produced cellulose material of the present invention is more advantageous in drying ability and secondary processing performance than the known so-called bacteria cellulose.

EXAMPLE 8

A culture was carried out at 15° C. for 4 days according to the culture method described in Example 1, using a method of adding a glucose solution on a step-by-step basis, so that the concentration of glucose in the medium was 1%. At a temperature of 15° C., little cellulose material was produced. After a culture solution was sterilized under a high pressure, a slightly produced cellulose material was separated and removed with a screen mesh (50 mesh) and bacteria were sedimentarily removed by centrifugal separation. A culture filtrate was condensed to half the original volume and then put into an acetone solution having a volume three times as large as that of the condensed filtrate while agitating the same. The resulting sediment was filtered with a screen mesh. The filtered matter was dissolved in water again in a concentration of 10%. This solution did not easily generate a precipitate with the addition of methanol and ethanol. Residues were removed from the re-dissolved solution. The precipitate was then settled again with acetone having a volume three times as large as the solution. The filtered matter was washed with a water/methanol mixture (30% methanol) to obtain a desired material. The composition of constitutional sugars of the desired material is shown in Table 2. It was found that the desired material had galactose, fucose and glucose as the main components and contained an uronic acid component.

EXAMPLE 9

A culture was carried out in the same manner as in Example 1 using China-made beet molasses as a carbon source. The culture temperature was 30° C. After the culture was completed, the medium was sterilized by an autoclave at 120° C. for 20 minutes. The sterilized culture broth was dried as it was to obtain a mixture of a cellulose material and a group of water-soluble polysaccharides. The ratio of the cellulose material to the group of water-soluble polysaccharides (cellulose material/group of water-soluble polysaccharides) in the mixture was 6/5.

EXAMPLE 10 AND COMPARATIVE EXAMPLE 2

A cellulose material having a morphology similar to that shown in FIG. 1 was obtained in the same manner as in Example 1, except that glucose was used as a carbon source and the culture temperature was 40° C. (Example 10). The obtained cellulose material was filtered with a screen mesh, rinsed, compressed, then immersed in 1% NaCH solution, sterilized, then again neutralized, rinsed and compressed to obtain a floccular body containing water, in the same manner as in Example 1. The cellulose material was excellent in liquid permeability in the screen mesh, and therefore these steps of filtration, rinsing, compression and so on could be carried out quite easily. Thereafter, the floccular body was dried and crushed at the same time at 200 rpm for 140° C. using a biaxial kneader (KRC Kneader (trademark) manufactured by Kurimoto Ltd.). The resulting dried powder was dispersed in tetrahydrofuran (THF), and then polysulfone (molecular weight of 5,000) was dissolved therein. The percentage of polysulfone based on the total amount of THF, the cellulose material and polysulfone was 8 wt %, and the percentage of the cellulose material was 0.8 wt %. The obtained polysulfone solution/cellulose material dispersion liquid was cast on a glass plate in a thickness of 500 μm and dried to obtain a cellulose/polysulfone film. The linear expansion coefficient of the obtained film was 19 ppm/° C., which was about one-third of the linear expansion coefficient of polysulfone, i.e. 55 ppm/° C. The linear expansion coefficient of the cellulose material itself is 5 ppm/°C., and the linear expansion coefficient of an alloy material decreases and becomes closer to 5 ppm/° C. as the formation of a composite proceeds at a satisfactory level.

As Comparative Example 2, *Acetobacter* strains were cultured to obtain cellulose. Using standard conditions and a Hestrin-Schramm medium (see S. Hestrin and M. Schramm, Biochem, J., 58, 345 (1954)), the culture was carried out at pH of 6 and a temperature of 28° C. under aerated agitation. The cellulose material obtained in Comparative Example 2 was an indeterminate and scaly strip and partially gelated, so that it clogged the screen and thus was hard to pass through the steps of filtration, rinsing, compression and the like. The structure and composition of the cellulose material obtained in Comparative Example 2 is shown in Table 1. For the sugar composition, the glucose content was 100% and linkages were all β-1,4-linkages. The cellulose material had a high I$\alpha$ fraction, i.e. 69%, and a high plane orientation. Using the cellulose material obtained in Example 2, a cellulose/polysulfone film was obtained in the same manner as in Example 10. The linear expansion coefficient of the film was 35 ppm/° C., which was apparently larger than that of the film of the present invention. This is due to the fact that the surface activity (density of OH groups) of the cellulose material of the Comparative Example is so low that the formation of a composite is insufficient.

TABLE 1

| | Carbon source | Degree of crystallinity (%) | I$\alpha$ fraction (%) | Orientation of crystal plane (%) | Constitutional sugar components | | | | Linkage form 1-4 Linkage fraction (%) | Yield based on sugar (%) |
|---|---|---|---|---|---|---|---|---|---|---|
| | | | | | Glc | Gal | Man | Ara | | |
| Example 1 | Sucrose | 85 | 59 | 91 | 97.8 | 1.7 | 0.5 | 0 | 98 | 12 |
| | Glucose | 91 | 62 | 92 | 99.6 | 0.3 | 0.1 | 0 | 99 | 15 |
| | Beet molasses | 82 | 50 | 85 | 89.7 | 8.7 | 1.2 | 0.4 | 95 | 10 |
| Comparative Example 2 | Glucose | | 69 | 90 | 100 | 0 | 0 | 0 | 100 | 5 |

Glc: glucose,
Gal: galactose,
Man: mannose,
Ara: arabinose

TABLE 2

| | Constitutional sugar components (%) | | | | | | | |
|---|---|---|---|---|---|---|---|---|
| Carbon source | Rha | Rib | Man | Ara | Fuc | Gal | Xyl | Glc |
| Glucose | 0.5 | 0 | 2.9 | 0 | 33.6 | 33.0 | 0 | 30.1 |

Rha: rhamnose,
Rib: ribulose,
Man: mannose,
Ara: arabinose,
Fuc: fucose,
Gal: galactose,
Xyl: xylose,
Glc: glucose

INDUSTRIAL APPLICABILITY

A cellulose material of the present invention has a high surface activity of fibrous fibrils and is excellent as a material for composites and useful as a stabilization imparting agent for composition components, a separating medium for microfiltration and sheet/granular materials having a stabilized morphological structure, owing to its morphological characteristics. Furthermore, the cellulose material/inorganic substance composite of the present invention is equivalent in basic morphology to a non-composite type cellulose material, and can not only exhibit functions specific to the contained inorganic substances but also provides new functions resulting from its morphology, and is of great significance from an industrial viewpoint.

The case in which a deoxy derivative with the C6-methyl group in glucose such as fucose is incorporated in the chain, like the group of water-soluble polysaccharides of the present invention, is unique. If water-soluble polysaccharides are cross-linked with a general cross-linking agent, they will highly absorb water or other solvents to become a gel, and are easily used in a biocompatible material, a medium for DDS and an agent capable/incapable of recognizing cells if they are applied to the surface of other material or incorporated in other material and then molded. Furthermore, the group of water-soluble polysaccharides of the present invention has an excellent ability to disperse different materials and has a strong dispersion holding power in the presence of a salt, which is the problem that cellulose based dispersants always encounter. Thus, the group of water-soluble polysaccharides can be used for a wide range of industrial applications including cosmetics.

The cellulose material and the group of water-soluble polysaccharides are useful for preparation of alloys in combination with other materials, for example a polymer material, a metal and a metal oxide.

The invention claimed is:

1. A method for producing a cellulose material, wherein the cellulose material is a water-insoluble polysaccharide formed by β-1,4-type sugar chain linkages, obtained by culturing CJF002 strain microorganisms, mutants thereof or subculture microorganisms thereof, said method comprising inoculating a culture medium with at least one selected from the group consisting of CJF002 strain microorganisms, mutants thereof and subculture microorganisms thereof, and then culturing under agitation at a temperature of 20° C. to 45° C. using sugars as carbon source.

2. The method according to claim 1, wherein said sugars are molasses.

3. A method for producing a composite of a cellulose material comprising a polymer material(s) other than cellulose and/or a metal and/or a metal oxide, wherein the cellulose material is a water-insoluble polysaccharide formed by β-1,4-type sugar chain linkages, obtained by culturing CJF002 strain microorganisms, mutants thereof or subculture microorganisms thereof, said method comprising inoculating a culture medium with at least one selected from the group consisting of CJF002 strain microorganisms, mutants thereof and subculture microorganisms thereof, and then culturing the same under agitation with a polymer material other than the cellulose material and/or a metal and/or a metal oxide at a temperature of 20° C. to 45° C. using sugars as carbon source.

4. The method according to claim 3, wherein said sugars are molasses.

* * * * *